(12) United States Patent
Bonhoeffer et al.

(10) Patent No.: US 8,562,672 B2
(45) Date of Patent: Oct. 22, 2013

(54) APPARATUS FOR TREATMENT OF CARDIAC VALVES AND METHOD OF ITS MANUFACTURE

(75) Inventors: Philippe Bonhoeffer, London (GB); Debra Ann Taitague, Orange, CA (US)

(73) Assignee: Medtronic, Inc., Minneapolis, MN (US)

( * ) Notice: Subject to any disclaimer, the term of this patent is extended or adjusted under 35 U.S.C. 154(b) by 1151 days.

(21) Appl. No.: 11/282,275

(22) Filed: Nov. 18, 2005

(65) Prior Publication Data

US 2006/0206202 A1  Sep. 14, 2006

Related U.S. Application Data

(60) Provisional application No. 60/629,468, filed on Nov. 19, 2004.

(51) Int. Cl.
*A61F 2/24* (2006.01)

(52) U.S. Cl.
USPC ...................................................... 623/2.11

(58) Field of Classification Search
USPC ........... 623/2.11, 1.26, 1.24, 2.14, 2.19, 1.11, 623/1.12, 1.15, 1.47, 1.49
See application file for complete search history.

(56) References Cited

U.S. PATENT DOCUMENTS

| | | |
|---|---|---|
| 3,334,629 A | 8/1967 | Cohn |
| 3,409,013 A | 11/1968 | Berry |
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |

(Continued)

FOREIGN PATENT DOCUMENTS

| | | |
|---|---|---|
| DE | 36 40 745 | 6/1987 |
| DE | 195 32 846 | 3/1997 |

(Continued)

OTHER PUBLICATIONS

Bonhoeffer, et al., "Percutaneous Insertion of the Pulmonary Valve," Journal of the Amer. College of Cardiology, 2002; 39:1664-1669.

(Continued)

*Primary Examiner* — Ryan Severson
*Assistant Examiner* — Julie A Szpira (57) ABSTRACT

A prosthetic valve including a replacement valve having a tubular valve body wall, an expandable stent having a framework with first and second ends, and suturing holding the framework to the valve body at the first and second ends. The suturing at the first end is colored differently from the suturing at the second end.

20 Claims, 7 Drawing Sheets

(56) References Cited

U.S. PATENT DOCUMENTS

| | | |
|---|---|---|
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,336,258 A * | 8/1994 | Quintero et al. ............... 623/2.1 |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,480,424 A | 1/1996 | Cox |
| 5,489,294 A | 2/1996 | McVenes et al. |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,817,126 A | 10/1998 | Imran |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,851,210 A * | 12/1998 | Torossian ................... 606/108 |
| 5,855,597 A * | 1/1999 | Jayaraman ................... 623/1.16 |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,051,014 A | 4/2000 | Jang |
| 6,059,809 A | 5/2000 | Amor et al. |
| 6,110,201 A | 8/2000 | Quijano et al. |
| 6,123,723 A | 9/2000 | Konya et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,164,339 A | 12/2000 | Greenhalgh |
| 6,168,614 B1 | 1/2001 | Andersen et al. |
| 6,171,335 B1 | 1/2001 | Wheatley et al. |
| 6,192,944 B1 | 2/2001 | Greenhalgh |
| 6,200,336 B1 | 3/2001 | Pavcnik et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,327,772 B1 | 12/2001 | Zadno-Azizi et al. |
| 6,338,735 B1 | 1/2002 | Stevens |
| 6,348,063 B1 | 2/2002 | Yassour et al. |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |

(56) References Cited

U.S. PATENT DOCUMENTS

| | | |
|---|---|---|
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,559,603 B2 | 5/2003 | Iwami |
| 6,562,058 B2 | 5/2003 | Seguin et al. |
| 6,569,196 B1 | 5/2003 | Vesely |
| 6,582,462 B1 | 6/2003 | Andersen et al. |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,622,604 B1 | 9/2003 | Chouinard et al. |
| 6,627,873 B2 | 9/2003 | Tchakarov et al. |
| 6,632,243 B1 | 10/2003 | Zadno-Azizi et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,792,979 B2 | 9/2004 | Konya et al. |
| 6,797,000 B2 * | 9/2004 | Simpson et al. ............. 623/2.15 |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,011,681 B2 | 3/2006 | Vesely |
| 7,041,128 B2 | 5/2006 | Mcguckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,115,141 B2 | 10/2006 | Menz et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,384,411 B1 | 6/2008 | Condado |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044591 A1 | 11/2001 | Stevens et al. |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0077696 A1 | 6/2002 | Zadno-Azizi et al. |
| 2002/0095209 A1 | 7/2002 | Zadno-Azizi et al. |
| 2002/0111674 A1 | 8/2002 | Chouinard et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0177890 A1 * | 11/2002 | Lenker ........................ 623/1.12 |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130729 A1 | 7/2003 | Paniagua et al. |
| 2003/0149475 A1 | 8/2003 | Hyodoh et al. |
| 2003/0149476 A1 | 8/2003 | Damm et al. |
| 2003/0149477 A1 * | 8/2003 | Gabbay ........................ 623/2.14 |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0199913 A1 | 10/2003 | Dubrul et al. |
| 2003/0199963 A1 | 10/2003 | Tower et al. |
| 2003/0199971 A1 * | 10/2003 | Tower et al. ................. 623/1.24 |
| 2003/0199972 A1 | 10/2003 | Zadno-Azizi et al. |
| 2003/0212410 A1 | 11/2003 | Stenzel et al. |
| 2003/0212452 A1 | 11/2003 | Zadno-Azizi et al. |
| 2003/0212454 A1 | 11/2003 | Scott et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |

(56) References Cited

U.S. PATENT DOCUMENTS

| | | |
|---|---|---|
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Seguin et al. |
| 2004/0093075 A1 | 5/2004 | Kuehne |
| 2004/0097788 A1 | 5/2004 | Mourles et al. |
| 2004/0098112 A1 | 5/2004 | DiMatteo et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Lobbi |
| 2004/0193261 A1 | 9/2004 | Berreklouw |
| 2004/0210240 A1 | 10/2004 | Saint |
| 2004/0210304 A1* | 10/2004 | Seguin et al. ............ 623/2.11 |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0225355 A1 | 11/2004 | Stevens |
| 2004/0254636 A1 | 12/2004 | Flagle et al. |
| 2004/0260317 A1 | 12/2004 | Bloom et al. |
| 2004/0260394 A1 | 12/2004 | Douk et al. |
| 2004/0267357 A1 | 12/2004 | Allen et al. |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0148997 A1 | 7/2005 | Valley et al. |
| 2005/0165477 A1 | 7/2005 | Anduiza et al. |
| 2005/0187616 A1 | 8/2005 | Realyvasquez |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0247763 A1 | 11/2006 | Slater |
| 2006/0259134 A1 | 11/2006 | Schwammenthal et al. |
| 2006/0259137 A1 | 11/2006 | Artof et al. |
| 2006/0271081 A1 | 11/2006 | Realyvasquez |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004688 A1 | 1/2008 | Spenser et al. |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0133003 A1 | 6/2008 | Seguin et al. |
| 2008/0147105 A1 | 6/2008 | Wilson et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0215144 A1 | 9/2008 | Ryan et al. |

(56) References Cited

U.S. PATENT DOCUMENTS

FOREIGN PATENT DOCUMENTS

| | | |
|---|---|---|
| DE | 195 46 692 | 6/1997 |
| DE | 198 57 887 | 7/2000 |
| DE | 199 07 646 | 8/2000 |
| DE | 10049812 | 4/2002 |
| DE | 10049813 | 4/2002 |
| DE | 10049814 | 4/2002 |
| DE | 10049815 | 4/2002 |
| EP | 0144167 | 6/1985 |
| EP | 0597967 | 12/1994 |
| EP | 0850607 | 7/1998 |
| EP | 1057459 A1 | 6/2000 |
| EP | 1 057 460 A1 | 12/2000 |
| EP | 1088529 | 4/2001 |
| EP | 0937439 B1 | 9/2003 |
| EP | 1340473 | 9/2003 |
| EP | 1356793 | 10/2003 |
| EP | 0819013 | 6/2004 |
| EP | 1472996 | 11/2004 |
| FR | 2788217 | 12/1999 |
| GB | 2056023 | 3/1981 |
| SU | 1271508 | 11/1986 |
| WO | 91/17720 | 11/1991 |
| WO | 92/17118 | 10/1992 |
| WO | 93/01768 | 2/1993 |
| WO | 93/15693 | 8/1993 |
| WO | 95/04556 | 2/1995 |
| WO | 95/29640 | 11/1995 |
| WO | 96/14032 | 5/1996 |
| WO | 98/14137 | 4/1998 |
| WO | 98/29057 | 7/1998 |
| WO | 98/36790 | 8/1998 |
| WO | 99/12483 | 3/1999 |
| WO | 99/33414 | 7/1999 |
| WO | 99/40964 | 8/1999 |
| WO | 99/47075 | 9/1999 |
| WO | 00/09059 | 2/2000 |
| WO | 00/41652 | 7/2000 |
| WO | 00/44308 | 8/2000 |
| WO | 00/44313 | 8/2000 |
| WO | 00/47136 | 8/2000 |
| WO | 00/47139 | 8/2000 |
| WO | 00/67661 | 11/2000 |
| WO | 01/05331 | 1/2001 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 01/97715 | 12/2001 |
| WO | 02/36048 | 5/2002 |
| WO | 02/41789 | 5/2002 |
| WO | 02/43620 | 6/2002 |
| WO | 02/47575 | 6/2002 |
| WO | 02/060352 | 8/2002 |
| WO | 02/036048 | 10/2002 |
| WO | 02/100297 | 12/2002 |
| WO | 03/003943 | 1/2003 |
| WO | WO 03/003949 | 1/2003 |
| WO | 03/011195 | 2/2003 |
| WO | 03/028592 | 4/2003 |
| WO | 03/030776 | 4/2003 |
| WO | 03/037227 | 5/2003 |
| WO | 03/015851 | 11/2003 |
| WO | 03/094793 | 11/2003 |
| WO | 2004/019811 | 3/2004 |
| WO | 2004/019825 | 3/2004 |
| WO | 2004/023980 | 3/2004 |
| WO | 2004/041126 | 5/2004 |
| WO | 2004/047681 | 6/2004 |
| WO | 2004/058106 | 7/2004 |
| WO | 2004/089250 | 10/2004 |
| WO | 2004/089253 | 10/2004 |
| WO | 2004/093728 | 11/2004 |
| WO | 2004/105651 | 12/2004 |
| WO | 2005/002466 | 1/2005 |
| WO | 2005/004753 | 1/2005 |
| WO | 2005/009285 | 2/2005 |
| WO | 2005/011534 | 2/2005 |
| WO | 2005/011535 | 2/2005 |
| WO | 2005/023155 | 3/2005 |
| WO | 2005/027790 | 3/2005 |
| WO | WO 2005/046528 | 5/2005 |
| WO | 2008/100599 | 8/2008 |

OTHER PUBLICATIONS

Bonhoeffer, et al., "Transcatheter Replacement of a Bovine Valve in Pulmonary Position," Circulation, 2000; 102:813-816.
Khambadkone, et al., "Percutaneous Pulmonary Valve Implantation in Humans," Circulation, 2005, 112(8):1189-1197.
Andersen, H.R. et al, "Transluminal implantation of artificial heart valves. Description of a new expandable aortic valve and initial results with implantation by catheter technique in closed chest pigs." Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Mitral Valve Dilatation with the Multi-Track System," Catheterization and Cardiovascular Interventions—Official Journal of the Society for Cardiac Angiography & Interventions (United States), Oct. 1999, pp. 178-183.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Technique and Results of Percutaneous Mitral Valvuloplasty With the Multi-Track System," Journal of Interventional Cardiology (United States), 2000, pp. 263-268.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Closure of a Paravalvular Mitral Regurgitation with Amplatzer and Coil Prostheses," Archives des Maladies du Coeur Et Des Vaisseaux (France), May 2002, pp. 483-486.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

(56) References Cited

OTHER PUBLICATIONS

Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Yonga, et al, "Effect of Percutaneous Balloon Mitral Valvotomy on Pulmonary Venous Flow in Severe Mitral Stenosis," East African Medical Journal (Kenya), Jan. 1999, pp. 28-30.
Yonga, et al, "Percutaneous Transluminal Balloon Valvuloplasty for Pulmonary Valve Stenosis: Report on Six Cases," East African Medical Journal (Kenya), Apr. 1994, pp. 232-235.
Yonga, et al, "Percutaneous Transvenous Mitral Commissurotomy in Juvenile Mitral Stenosis," East African Medical Journal (Kenya), Apr. 2003, pp. 172-174.
Boudjemline, et al., "Images in Cardiovascular Medicine, Percutaneous Aortic Valve Replacement in Animals," Circulation (U.S.), Mar. 16, 2004; 109, p. e161.
Yonga, et al, "Percutaneous Balloon Mitral Valvotomy: Initial Experience in Nairobi Using a New Multi-Track Catheter System," East African Medical Journal (Kenya), Feb. 1999, pp. 71-74.

* cited by examiner

APPARATUS FOR TREATMENT OF CARDIAC VALVES AND METHOD OF ITS MANUFACTURE

CROSS REFERENCE TO RELATED APPLICATIONS

This application claims priority to U.S. Provisional application having Ser. No. 60/629,468 filed Nov. 19, 2004, entitled "APPARATUS FOR TREATMENT OF CARDIAC VALVES AND METHOD OF ITS MANUFACTURE," which application is incorporated herein by reference in its entirety.

TECHNICAL FIELD

The invention relates generally to treatment of cardiac valve disease and more particularly to replacement of malfunctioning pulmonary valves.

BACKGROUND

Recently, there has been increasing interest in minimally invasive and percutaneous replacement of cardiac valves. In the context of pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. The replacement valve is mounted on a balloon catheter and delivered percutaneously via the vascular system to the location of the failed pulmonary valve and expanded by the balloon to compress the valve leaflets against the right ventricular outflow tract, anchoring and sealing the replacement valve. As described in the articles: *Percutaneous Insertion of the Pulmonary Valve*, Bonhoeffer, et al., Journal of the American College of Cardiology 2002; 39: 1664-1669 and *Transcatheter Replacement of a Bovine Valve in Pulmonary Position*, Bonhoeffer, et al., Circulation 2000; 102: 813-816, the replacement pulmonary valve may be implanted to replace native pulmonary valves or prosthetic pulmonary valves located in valved conduits. Surgical procedures for percutaneous pulmonary valve implantation are described in Khambadkone et al., *Percutaneous Pulmonary Valve Implantation in Humans*, Circulation, Pp. 1189-1197 (Aug. 23, 2005).

Other implantables and implant delivery devices are disclosed in published U.S. Patent Application No. 2003-0036791-A1 and European Patent Application No. 1 057 460-A1.

SUMMARY

The present invention is particularly directed to valves of the type generally described in the Tower et al. and Bonhoeffer, et al. references cited above as used within a prosthetic valve or valve system. However, the invention may also be useful in other types of valves, particularly valves which take the form of a generally tubular valve body of natural or synthetic material, in which valve leaflets are provided. Examples of such other valves include those described in U.S. Pat. Nos. 6,719,789 and 5,480,424, both issued to Cox.

In one aspect of the invention, an improved suturing technique is employed to attach the valved venous segment or other replacement valve to its associated stent. In at least one aspect, in order to prevent inward bowing of the walls of the venous segment or other substantially tubular valve body, the tissue of the segment or other tubular valve body is attached to the stent at all or substantially all of the angled portions of the stent. Alternatively, sutures may be distributed about the stent at other locations such that no portion of the venous wall or other tubular valve body is more than a few millimeters from a suture.

In another aspect of the invention a prosthetic valve is provided that includes a replacement valve having a substantially tubular valve body wall, an expandable stent having a framework including a plurality of "V" structures, each having a base, and sutures located at each base holding the valve body wall to the stent. The sutures are preferably no further than 7 mm from one of the sutures. The replacement valve can be a valved vein segment and the valve body wall can be the vein segment's wall. The valved vein segment can be a valved segment of bovine jugular vein.

In another aspect of the invention, an assembly consisting of a venous segment or other replacement valve and an associated stent is color-coded to allow for easier determination of a particular configuration. For example, such a visual indicator can be used to identify which end of the valve is the inflow end and which end of the valve is the outflow end. In a particularly preferred embodiment, the suturing at the outflow end and/or inflow end of the valve is colored to match that portion of an associated delivery device intended to be adjacent the end of the valve when properly mounted to the device. Other methods of providing a colored marking may be provided in addition to or in substitution for sutures.

In another aspect of the invention, a prosthetic valve and delivery system is provided, with the valve being mountable to the delivery system in correct or incorrect manners. The prosthetic valve comprises a replacement valve having a substantially tubular valve body wall, an expandable stent having a framework with first and second ends, and sutures holding the framework to the valve body wall at the first and second ends. The sutures at the first end are colored differently from the suturing at the second end. The delivery system is provided with a colored component of generally the same color as the sutures at the first end of the framework and the colored component is located such that when the valve is correctly mounted to the delivery system, the colored component is adjacent to the first end of the framework. Alternatively, the system may be provided with a colored marker located at one of the first and second ends of the framework, rather than the colored sutures. When the valve is correctly mounted to the delivery system, the colored component is adjacent to the colored marker. In a further alternative, the replacement valve (rather than the stent framework) has first and second ends, wherein one of the ends includes a colored marker that is located relative to the delivery system such that when the valve is correctly mounted, the colored component is adjacent to the colored marker.

BRIEF DESCRIPTION OF THE DRAWINGS

The present invention will be further explained with reference to the appended Figures, wherein like structure is referred to by like numerals throughout the several views, and wherein:

FIGS. 5-11 illustrate several exemplary sequential steps that can be performed in providing an assembly including a stent and a venous segment, where each of these Figures is summarized in further detail as follows:

DETAILED DESCRIPTION

Figure 1:
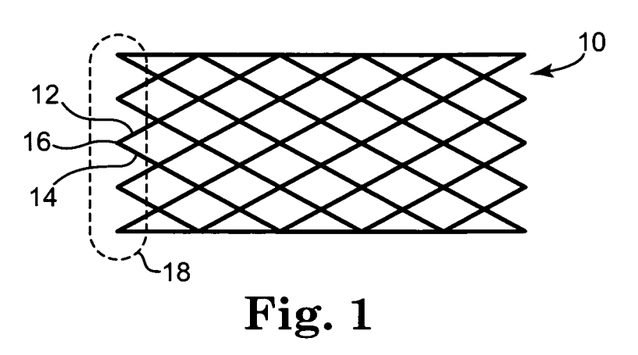
FIG. 1 is a top perspective view of an exemplary stent for use in conjunction with the present invention.

Referring now to the Figures, wherein the components are labeled with like numerals throughout the several Figures, and initially to FIG. 1, one configuration of an exemplary stent 10 for use in conjunction with the present invention is illustrated. The stent 10 as illustrated corresponds generally to a stent of the type described in the above-cited Tower, et al., and Bonhoeffer et al. references, for example. The stent 10 may be fabricated of platinum, stainless steel or other biocompatible metal. Stent 10 may alternatively be fabricated using wire stock as described in the above-cited Tower, et al. applications, or the stent 10 may be produced by machining the stent from a metal tube, as is commonly employed in the manufacturing of stents. The number of wires, the positioning of such wires, and various other features of the stent can vary considerably from that shown in the figures. The stent can be used in conjunction with bovine jugular vein segments in which the stent would typically be in the range of about 16 mm to 20 mm in diameter when expanded. The specifics of the stent can vary widely within the scope of the invention, such that many other known generally cylindrical stent configurations may be used and are considered to be within the scope of the invention.

The stent 10, like most expandable cylindrical stents, generally takes the form of a series of zig-zag ring structures, such as are indicated by reference number 18. The structures 18 are coupled longitudinally to one another to form a generally cylindrical-shaped structure, although it is understood that the structures 18 can form be arranged in an at least slightly oval or elliptical shape. Each ring structure 18 takes the form of a series of adjacent generally straight sections (e.g., 12, 14) which each meet one another at one end at a curved or angled junction (e.g., junction 16) to form a "V" or "U" shaped structure. For purposes of the present application, this structure will be referred to as a "V", and the included junction (e.g., junction 16) is referred to as the base of the "V". The relatively straight portions (e.g., straight sections 12, 14) of the stent between the bases of the "V"s, are referred to herein as the "arms" of the "V" or simply as "arms". While the angled junctions illustrated take the form of relatively sharply angled junctions, the "V" terminology is also intended to include more gradually curved junctions as well, such as might be shaped more like a "U" with arms that are angled away from each other at least slightly.

Stents of the type illustrated are generally sized to be in the 16 mm to 20 mm diameter range when expanded, and are configured so that the bases of the "V"s are preferably spaced no further than about 8 mm from one another around the circumference of the stent. It should also be understood that although the ring structures are coupled to one another at the base of each "V" in the illustrated embodiment, stents employed according to the present invention may employ ring structures coupled to one another at fewer bases of their "V"s or coupled to one another by additional and/or different structures, such as longitudinal members of the type disclosed in U.S. Pat. No. 6,773,455, issued to Allen, et al., U.S. Pat. No. 6,641,609, issued to Globerman and in U.S. Pat. No. 6,136,023, issued to Boyle. The invention also includes within its scope those stents in which wires are formed into zig-zags and wound spirally to produce a cylindrical structure, as in U.S. Pat. No. 6,656,219, issued to Wictor or woven stents as disclosed in U.S. Pat. No. 4,655,771, issued to Wallsten.

Stents of the type described above, such as stent 10, can be assembled into a pulmonary valve assembly in accordance with the methods of the invention described herein. The pulmonary valve assemblies can be utilized in for purcutaneous replacement of cardiac valves, for example. One exemplary method for assembling a stented valve generally first includes preparation of a vein segment, then a subsequent mounting or attachment of the prepared vein segment to the stent, which are described below in further detail.

Figure 2:
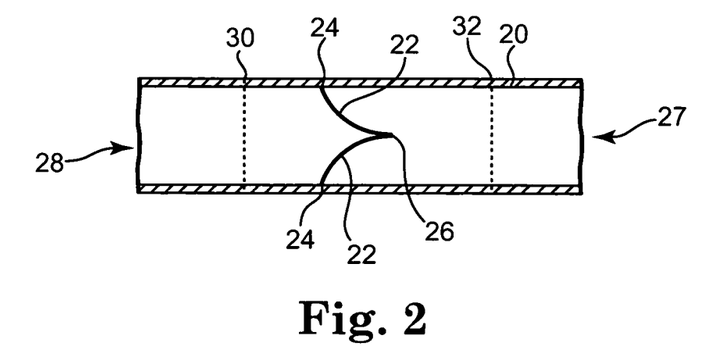
FIG. 2 is cross-sectional side view of an exemplary valved venous segment for use in conjunction with the present invention.

FIG. 2 illustrates a cross-sectional view of a vein segment 20 of the type that is appropriate for use in construction of the valve assembly. The embodiment illustrated may exemplify a preserved bovine jugular vein of the type described in the above-cited Bonhoeffer, et al. and Tower, et al. references, but other vessels or donor species may alternatively be employed. Alternatively, other replacement valves with substantially tubular valve bodies may be substituted. The vein segment 20 as illustrated includes leaflets 22 extending from the wall of the vein segment 20 from leaflet bases 24 (i.e., bottoms of leaflets 22) to commissures 26, which define the outer meeting points of the furthest downstream portions of the leaflets 22. The vein segments used for the present invention are generally referred to herein as being tubular or substantially tubular in shape, which are typical shapes in which vein segments are provided, although the vein segments can be somewhat irregular or differently shaped, such as elliptical or the like. In any case, the description of the vein segments or valves herein as being tubular or generally tubular is meant to encompass any such shapes. The vein segment 20 further includes an inflow end 28 through which blood will enter the vein segment 20 and an outflow end 27 through which blood will exit the vein segment 20.

The vein segment 20 preferably has three leaflets 22, but may optionally have less. The leaflets 22 of the vein segment 20, in their closed position, should have the capability to hold fluid for at least five seconds, and there should preferably be no branches in that portion of the vein wall which will ultimately be located in the stent.

In a particular procedure, a vein segment 20 of an appropriate length is selected for attachment to a desired stent. The wall of the vein segment 20 is then measured to determine its wall thickness. As described in the above-cited Bonhoeffer, et al and Tower, et al. references, for example, if the vein segment 20 has a wall thickness greater than about 0.5 mm, the vein segment 20 will preferably be thinned to leave a wall thickness of no more than about 0.5 mm. This thinning process may be performed in a variety of ways, one of which includes placing the vein onto a mandrel, then trimming the adventitial tissue. One method of performing the thinning includes pulling the adventitia from the wall of the vein, then using a cutting instrument, such as scissors, to snip or cut the tissue fibers until as much of the tissue fibers are removed as necessary to achieve a desired wall thickness. After the thinning process is complete, the tissue may appear to be relatively translucent.

Either prior to or subsequent to the thinning operation described above, the vein segment 20 can be trimmed to a desired length for attachment to a stent in order to easier perform the steps of securing the vein segment 20 to a stent 10. This step would not be necessary if the vein segment 20 has been provided in the desired length, such as from some type of preparation location. In at least one exemplary process in which vein segment trimming is desired, the vein segment 20 is trimmed at a first location 30 spaced from inflow end 28 and/or at a second location 32 spaced from output end 27 to leave a minimum of about 15 mm of tissue from the tops of the commissures 26 and the bottoms 24 of the leaflets 22 to the ends of the vein segment 20. If the vein segment 20 is trimmed in this way, the inflow end 28 and outflow end 27 will then be shifted to these new locations where the vein segment 20 was trimmed. It is understood that the distance from the tops of the commissures 26 and the bottoms 24 of the leaflets 22 to the ends 27, 28 can be more or less than 15 mm, as desired or necessary for attachment to differently sized stents, where the 15 mm distance is desirable and common for at least some valve assemblies. In any case, it is desirable to provide a long enough vein segment 20 to accomplish the remaining steps of the assembly method that is not so long that it interferes with the attachment procedure.

Figure 3:
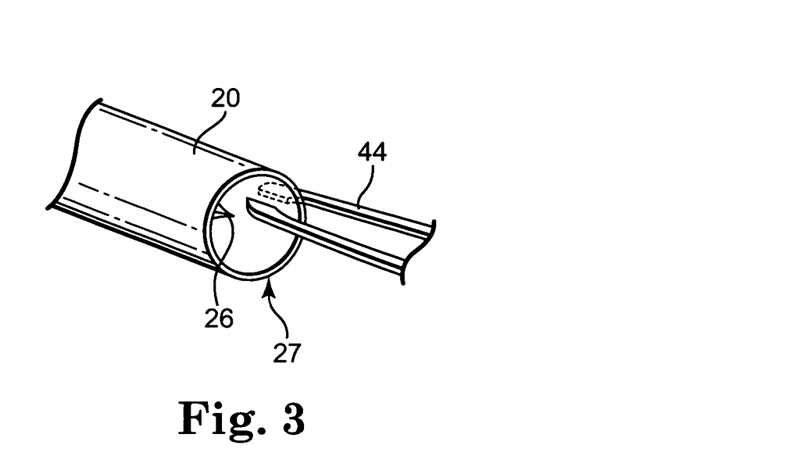
FIG. 3 is a perspective view of an exemplary method of marking the venous segment prior to beginning the process of suturing the venous segment to its associated stent.

Next, FIG. 3 illustrates one exemplary manner of locating and marking the top of each commissure 26 on the outside of the vein segment 20. First, a forceps 44 is positioned close to, but at a minimum of 1 mm above the top of each commissure 26 of vein segment 20. The forceps 44 are squeezed together to make an impression on the wall of the vein segment 20. This leaves a temporary mark 52 (see FIG. 4) on the outer wall of vein segment 20 to indicate where to place a suture. It is contemplated that other tools or methods may be used to provide a mark in a similar location on the outside of the vein segment 20.

Figure 4:
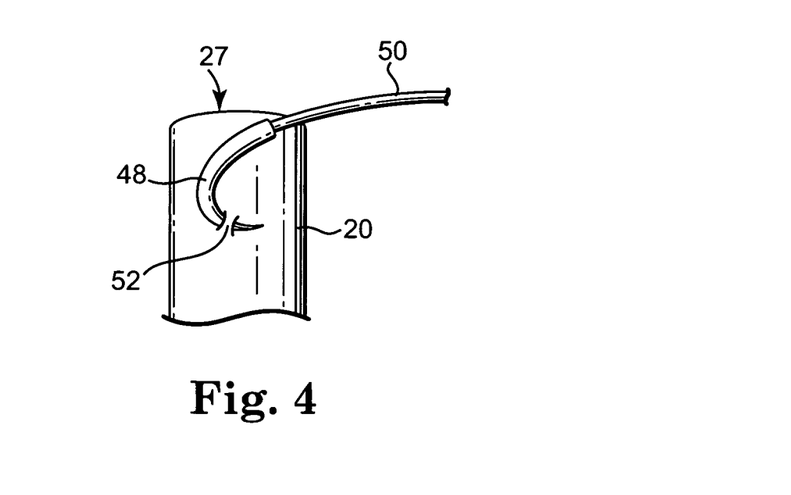
FIG. 4 is a top view of an exemplary method for placing of sutures for marking the position of valve commissures of the venous segment, such as the venous segment of FIG. 3.

Next, as is illustrated in FIG. 4, a needle 48 is carefully inserted into each marked area 52 of the vein segment 20. Needle 48 is preferably threaded with a colored suture material 50. In a desired method, the needle 48 should not extend through the entire thickness of the vein segment 20, but should only penetrate through a portion of the thickness of vein segment 20. After bringing the suture 50 through the marked area 52, the suture 50 is loosely secured, such by tying it into a very loose square knot 54 (see FIG. 5) or by using another securing technique that allows a temporary positioning of the suture 50. The process of marking the outside of the vein segment 20 and providing a temporary suture should be performed in the area of each of the commissures 26. The vein segment 20 is now prepared for mounting to the stent 10.

If an alternative replacement material for valves is employed instead of a bovine jugular vein segment, it will be prepared for mounting to the stent as appropriate for the particular valve chosen. For example, it may be prepared as described in the above-cited patents issued to Cox. Thus, the particular preparation techniques described above may not be necessary for all types of vein segments, although it is desirable that other types of vein segments are provided with some type of marking on its outer surface to indicate the location of the commissures.

One exemplary method of mounting the vein segment 20 or other replacement valve to the stent 10 is described below with particular reference to FIGS. 5-11. The suturing procedure described may be performed on a mandrel or while simply manually holding the vein segment 20 or other replacement valve. Use of a mandrel is particularly applicable if a bovine valved venous segment is employed, but may or may not also be appropriate for other replacement valves. In the below description of an exemplary process, however, a mandrel is described for use in the mounting procedure.

Figure 5:
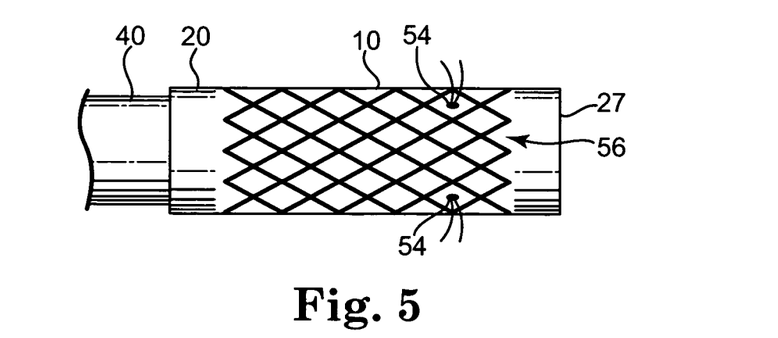
FIG. 5 is a top view of an assembly showing an exemplary initial placement of a stent over the venous segment, with both elements positioned on a mandrel.

First, as illustrated in FIG. 5, the vein segment 20 is slid partially onto a mandrel 40 (e.g., for about ¼ of the length of the vein segment 20), so that the outflow end 27 extends beyond the end of the mandrel 40. The stent 10 is placed over or around the vein segment 20 so that an outflow portion 56 of the stent 10 overlies knots 54, which were made as described above in conjunction with FIG. 4. The mandrel 40 is then slid further through the vein segment 20 and stent 10. The vein segment 20 may stretch to accommodate the outer diameter of the mandrel 40, which may be at least slightly larger than the inner diameter of the vein segment 20. It may be necessary in some cases to temporarily stop the movement of the mandrel 40 through the vein segment 20 in order manually adjust the stent 10 to keep it properly positioned relative to the vein segment 20 and to accommodate any stretching. In any case, the mandrel 40 is then moved further relative to the vein segment 20 and stent 10 until the outflow end 27 of vein segment 20 no longer extends past the end of mandrel 40.

Figure 6:
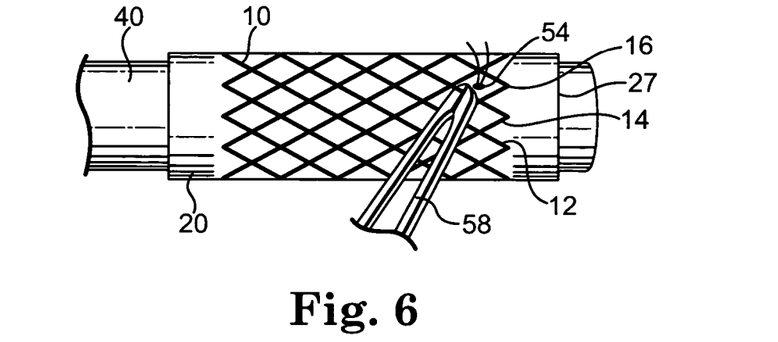
FIG. 6 is a top view of the assembly of the type illustrated in FIG. 5, and further illustrating an exemplary final positioning of the venous segment relative to the stent.

FIG. 6 shows the vein segment 20 and stent 10 as positioned completely on the mandrel 40. At this point, the stent 10 can be adjusted to achieve a desired position of the stent 10 relative to the vein segment 20 and its associated structure (e.g., the commissures 26). In order to adjust the position of stent 10, a tool such as a dull-tipped forceps 58, for example, can be used to gently move the tissue of the vein segment 20 so that the locations of the commissure tops (which were previously marked by knots 54), are in a desired position relative to the stent 10. In one exemplary embodiment, the knots 54 and corresponding tops of commissures 26 will be positioned at least 1 mm away from the base 16 of the nearest "V" and at least 1 mm away from the adjacent arms 12, 14 of the stent 10. This positioning of the vein segment 20 will help avoid stitching the arms 12, 14 and/or base portion 16 of the "V" portions into the leaflets 22. The tops of the commissures 26 and the leaflets 22 are then preferably positioned within the frame of the stent 10. In order to verify the positioning of the vein segment 20, a light source can optionally be used to view the components, such as can be accomplished by using the room light as back lighting. However, if the vein segment 20 is manipulated to the point that it twists the commissures 26 or distorts the leaflets 22, the vein segment may need to be further examined and adjusted or replaced.

Figure 7:
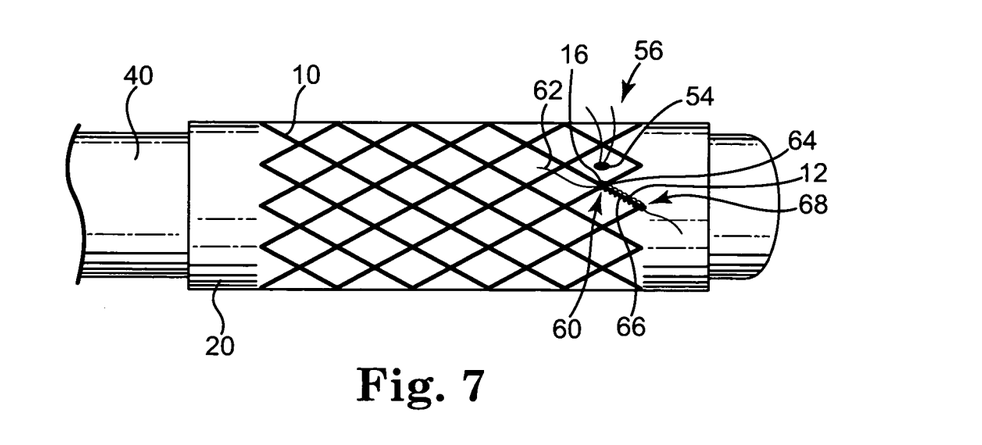
FIG. 7 is a top view of the assembly of the type illustrated in FIG. 6, and further illustrating a technique of suturing the ends of the stent to the venous segment.
Figure 8:
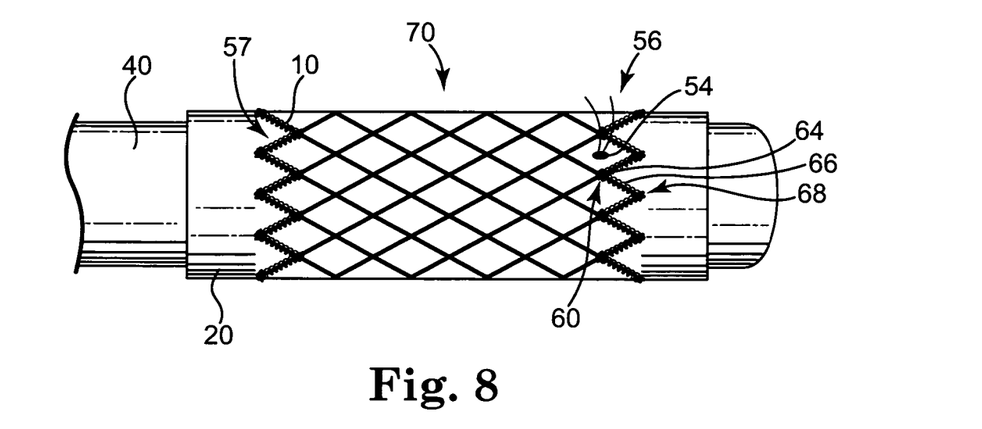
FIG. 8 is a top view of an assembly of the type illustrated in FIG. 7, and further illustrating both of the stent ends secured to the vein segment.

After the vein segment 20 is positioned as desired relative to the stent 10, an area of the stent 10 nearest the outflow end 27 of vein segment 20 (which may be referred generally to as an outflow end 56 of the stent 10) will then be sutured or attached to the vein segment 20, as illustrated in FIG. 7. In this suturing process, the suture material used is preferably easily visible to the human eye, and visually distinct such as may be provided by a suture material having a color that is at least somewhat darker or lighter in color than the vein segment 20 and/or the stent 10. For example, the suture material may be provided as a blue, 5-0 suture material. The suture material may be provided as a monofilament or multifilament structure made of natural or synthetic materials (e.g., nylon or polypropylene), or may alternatively include an elongated metal or metal-composite thread or filament or any other material that is suitable for permanently securing the stent to a vein segment in accordance with the present invention. The suture material is threaded onto a needle for the suturing process.

To begin the suturing process, suture material is threaded into the vein segment 20 under one side of the base 16 of a "V" at a location 60. The suture is then pulled through to the opposite side of the base 16 of the "V", preferably leaving an extending tail 62 of suture material, which may be approximately 2 cm in length, for example. The suture material is then made into a loop and the needle is threaded through the loop. The two ends of suture material are then pulled to make a locking knot 64 around the stent 10 at the base 16 of one of the "V"s. While it is important to pull the knot relatively tight, the knot should not be pulled so tight that it bends the wire of the stent 10. The suture is then looped around one arm 12 of the "V", such as at a location 66, by inserting the needle through the vein segment 20 under the stent 10 and adjacent to the arm 12 and pulling the suture taut. This creates a first whipstitch around the arm 12. The described step of inserting the needle through the vein segment 20 under the stent 10 is preferably repeated at least 3 more times to create a total of at least 4 whipstitches around the arm 12. Although it is possible that more or less than 4 whipstitches can be used along a particular arm 12, the number of stitches used should be sufficient to provide secure attachment of each arm 12, 14 of the stent 10 to the vein segment 20. Each sequential placement of a whipstitch is positioned at a progressively further distance from the locking knot 64. At the same time, each of these whipstitches will be placed at a distance that is progressively closer to the base of an adjacent "V" at the opposite end of the arm 12, such as is illustrated as a location 68.

Once the next base of a "V" is reached at 68, another locking stitch should be made around the stent 10 by again making a loop with the suture, pulling the thread through the loop, and tightening the knot around the base 16 at location 68. The locking stitch at the base 16 of each "V" should also be secured to the vein segment 20 by passing the thread at least partially through the vein segment 20 during the process of making the locking stitch. These steps will then be repeated along each of the arms 12, 14 around the outflow end 56 of the stent 10 until the suture tail 62 is reached. That is, a series of preferably at least 4 whipstitches should be made along each of the arms 12, 14 around the circumference of stent 10, with a locking stitch at each base 16, although it is possible that less than 4 whipstitches can be used along one or more of the arms 12, 14. The whipstitches are preferably continuous and uninterrupted around the circumference of stent 10.

Once the suture tail 62 is reached, a final locking stitch is made. To do this, the suture tail 62 is preferably tied off with a double throw square knot by wrapping the longer suture tail twice around the tool used to hold the needle (e.g., a needle holder resembling pliers) and pulling the shorter suture tail through the loops. The tying off process is preferably finalized by making a single throw square knot by wrapping the longer suture tail once around the needle holder and pulling the shorter suture tail through the loop. The knots should both be tightened to provide a more secure attachment. The shorter suture tail is then trimmed at a location close to the stent 10, preferably without cutting into any of the stitches or tissue. The suture is then preferably threaded under the stent 10 to pull the knot behind the stent 10. The suture can be trimmed relatively close to the stent 10. At this point, the structure includes stitching extending completely around the outflow end 56 of the stent 10.

While the above description provides one sequence of suture loops and knots for securing the suture material, a different series of knots and suture manipulation may alternatively be utilized, so long as such process provides a secure attachment of the stent to the vein segment along the various segments of the stent described herein. In particular, the knots and stitches provided in the suture should not be capable of disengaging from the stent and/or vein segment and should not interfere with the leaflets of the vein segment.

The above steps are then repeated at the inflow end 57 of the stent 10 using a suture material that is visually distinct from the suture used at the outflow end 56 of stent 10. For one example, white or clear 5-0 suture material can be used to stitch the vein segment 20 to the inflow end 57 of the stent 10 to produce a stented valve. The suture material used at the inflow end 57 may be the same as or different from the suture material used at the outflow end 56, which may also be the same as or different from the suture material used at any additional locations where sutures are used to attach the stent to the vein segment. The structure is illustrated as a stented valve 70 in FIG. 8, which shows a stent 10 that is stitched to the vein segment 20 around the circumference of both its inflow end 57 and its outflow end 56. Although it is possible in another exemplary method of the invention to stitch the inflow end 57 to vein segment 20 before stitching the outflow end 56 to vein segment 20, another procedure and/or device would need to be used to insure that the outflow end 56 will remain properly positioned relative to the commissures 26 during the process of stitching the inflow end 57.

The use of different colored sutures at the inflow end 28 and outflow end 26 of the stent 10 can assist a physician in mounting the stented valve in its proper orientation to its delivery device, as discussed below. In the event that alternative replacement valves are employed, the locations of the colored sutures may differ from that described above, but they preferably should be located at or adjacent to the inflow and/or outflow ends of the valve. Similarly, if alternative stents are employed, the particular stitching pattern may vary to accommodate the specific configuration of the stent. In any of these configurations, however, a visual indicator at one end of the stent and/or vein segment is preferably used to be sure to achieve the correct orientation of the valve relative to the delivery device with which it will be used.

Figure 9:
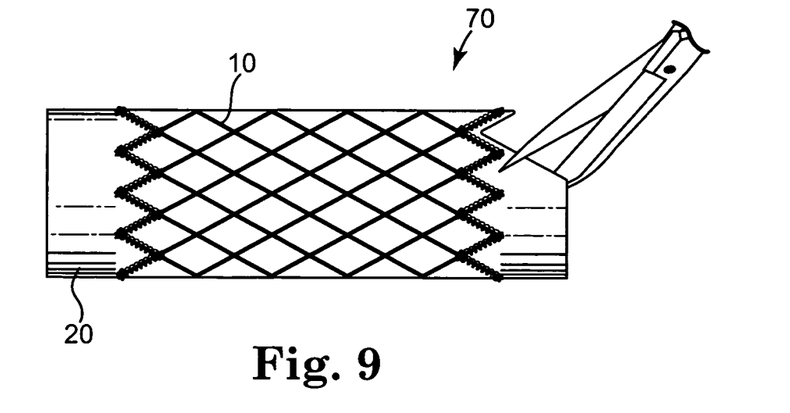
FIG. 9 is a top view of an assembly of the type illustrated in FIG. 8 and further illustrating an exemplary technique for trimming the venous segment to the approximate length of the stent.
Figure 10:
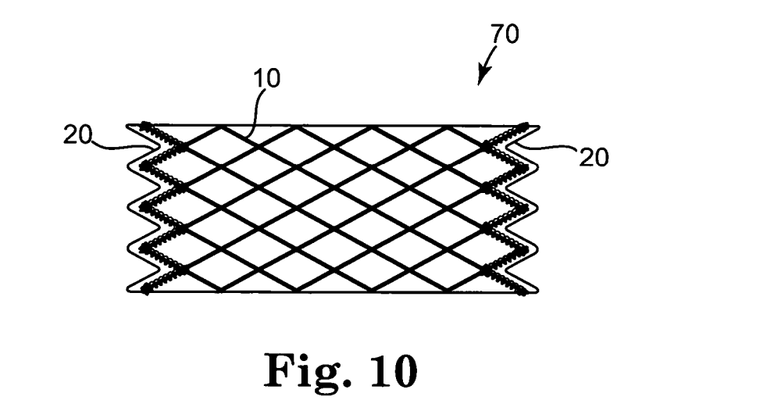
FIG. 10 is a top view of an assembly of the type illustrated in FIG. 9 and further showing the venous segment after being trimmed to match the stent.

Following the procedure of stitching the stent 10 to the vein segment 20, the stented valve 70 is removed from the mandrel 40. The edges of the vein segment 20 that extend beyond the stent 10 are then trimmed to generally follow the contour of the edges of stent 10, as illustrated in FIG. 9. In an exemplary process, the vein segment 20 is cut approximately 1 mm away from the frame of the stent 10 without cutting into any of the sutures. FIG. 10 illustrates the stented valve 70 after completion of the procedure. For replacement valves other than bovine jugular valve segments, this trimming operation may not be required.

Figure 11:
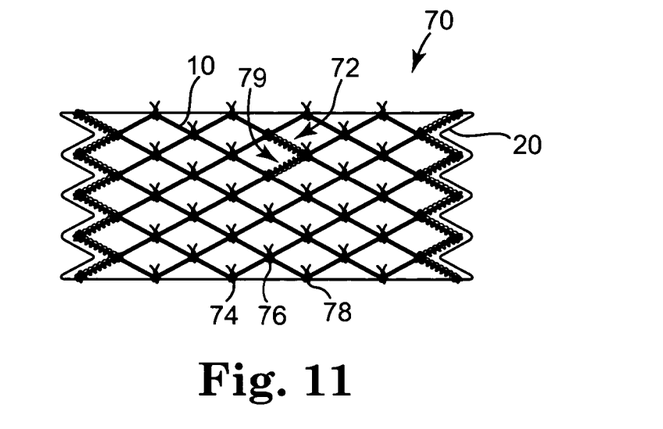
FIG. 11 is a top view of an assembly of the type illustrated in FIG. 10 and further illustrating the final steps of suturing the stent to the venous segment.

To provide for an even more secure attachment of the vein segment 20 to the stent 10 and to prevent or minimize inward bowing of the walls of the vein segment 20, suture material may be used to provide additional locations for attachment of the vein segment 20 to the stent 10. FIG. 11 illustrates such an exemplary attachment configuration, although all of the attachment locations shown may not be desirable or necessary for every stented valve. That is, either some or all of the additional attachment locations described below may be used for a stented valve.

With particular reference to FIG. 11, suture material is used to secure the vein segment 20 at each sinus area 72, which are each located generally between the commissures. Suture material can also be used to secure the vein segment 20 at substantially all or more preferably at the base of every "V" (e.g., at locations 74, 76, 78, etc.). The stented valve 70 is preferably not on a mandrel when making these stitches and the suture material used for these additional stitches is preferably clear, such as a 5-0 clear suture.

One exemplary method to secure the vein segment 20 in the sinus areas includes first locating the single "V" of the stent that is most centered in each sinus area 72. It is acceptable for the "V" chosen for stitching to point toward either outflow end 56 or inflow end 57 of stented valve 70. Starting at the base of this "V", the suture is threaded under the stent 10 and a single throw securing square knot is made, followed by a double throw securing knot. The vein segment 20 is then stitched to the arms of that "V" with preferably at least 4 whipstitches per arm and a locking stitch at the base of the "V" as described above in conjunction with suturing the vein segment 20 to the ends 56, 57 of the stent 10. As with the previously described securing processes, more or less than 4 whipstitches may be used, depending on a number of factors, including the size of the stent and the length of the arms that make up its structure. In any case, the number of stitches used should be sufficient to provide secure attachment of the stent portions to the vein segment. The suture is then tied off or terminated, preferably with three locking stitches. The resulting knot can be tucked behind the stent and the suture tails trimmed as close to the knot as possible. After stitches are provided along the length of both arms, the stented valve 70 will include a "V" shaped area 79 where the stent 10 is secured to the vein segment 20, as shown in FIG. 11. This process is preferably repeated for each sinus area of the stented valve 70. In this process, if the replacement valve is other than a bovine vein segment, securement of the valve body or vein segment to the stent in the sinus areas as illustrated may not be necessary or desirable.

Next, the vein segment is secured at the bases of some or all of the remaining "V"s of the stent using the following exemplary process: First, a suture is passed through the vein segment behind the base of the "V", taking care not to sew through the leaflets. A single throw knot is then made, followed with a two throw securing knot. The suture tails are then trimmed relatively close to the knot to minimize the length of extending suture material. This process is repeated for the base of each of the "V"s that is to be secured in this manner. When the desired "V" bases are sutured, there is preferably no portion of the vein wall or other tubular valve body wall more than 7 mm from a suture, and more preferably no more than 5 mm from a suture. The stented valve can then be sterilized and packaged.

By suturing the vein segment to the stent to all or substantially all of the bases of the "V"s, inward ballooning of the vein segment as described in the article: *Remblacement Valvulaire Pulmonaire par voie Percutanee: Vers une Modifiction de la Prothese*, Boudjemline, et al. Arch Mal Cour 2003: 96:461-6 may be avoided or controlled. With the methods and valves described herein, the suturing pattern assures that no point on the vein wall is more than about 5 mm from a supporting suture, particularly when all of the bases of the "V"s are secured to the vein segment. In stents as illustrated or in stents with other geometries, the same result could be obtained by ensuring that regardless of the specific stent element sutured to the vein segment, there are no areas of the vein wall or other tubular valve body wall that are more than 7 mm from a suture, and preferably that there are no areas of the vein wall or other tubular valve body wall more than 5 mm from a suture.

Figure 12:
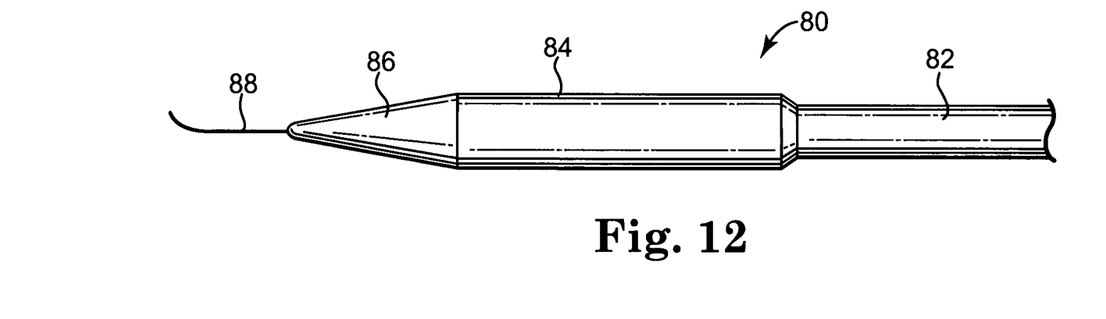
FIG. 12 is a top view of an exemplary delivery system for an assembled stented venous segment.

FIG. 12 illustrates a system for delivering a stented valve (e.g., the stented valve 70 of FIG. 11) to a desired implant location, such as the pulmonary vein, a valved conduit or other location. The delivery system 80 comprises an outer sheath 82 overlying an inner balloon catheter (not visible in this Figure). The outer sheath has an expanded distal portion 84, within which the stented valved venous segment is located. The stented valve is compressed around a single or double balloon located on the inner balloon catheter. A tapered tip 86 extends from the distal end of the inner balloon catheter and serves to ease the passage of the delivery system through the vasculature. The tapered tip 86 may be color-coded to match the color of the suture on the stented valve that will be used. For example, if a blue suture material is used nearest the end of the stented valve 70 that is to be closest to the tapered tip 86, the tapered tip 86 may also be blue in color in order to provide an easy visual indicator of the proper orientation of the valve 70. The system may also include a guidewire 88, which may be, for example, a 0.089 cm extra stiff guidewire as manufactured by Amplatzer, Golden Valley, Minn. The guidewire can be used to guide the delivery system to its desired implant location.

While the above description refers primarily to the use of colored suture material as a visual indicator for the orientation of a stented valve, another type of visual indicator, indicia, symbol or marker can be used in addition to or instead of the colored suture materials. For example, the delivery system can be provided with some type of symbol, indicia, pattern, or marker that matches or otherwise corresponds with a symbol, pattern, or color on one end of the stented valve to guide the user in properly orienting the stented valve relative to the delivery system. It is further possible that opposite ends of the stented valve are made to be visually distinct from each other through the use of the same or different suture materials that are routed or stitched differently on each end to provide a different visual effect. The corresponding delivery system includes some type of indicator that corresponds to one or both of the suture patterns to provide a guide to the proper orientation of the valved stent. In another alternate configuration, the stented valve itself may have a geometrical configuration at one or both of its ends that matches a feature or features on the delivery system to facilitate both proper placement and orientation of the stented valve relative to the delivery system. These described combinations of colors, materials, patterns, and other markers that can be used in accordance with the invention are exemplary configurations, where other combinations are possible that include at least one visual indicator on a stented valve that is provided to correspond with a visual indicator on its corresponding delivery system.

The delivery system and its use may correspond to that described in the above-cited Tower, et al. applications. The delivery system is advanced to the desired valve implant site using the guidewire 88, after which the sheath 82 can be retracted to allow balloon expansion of the venous segment, as illustrated in FIG. 13, as discussed below.

Figure 13:
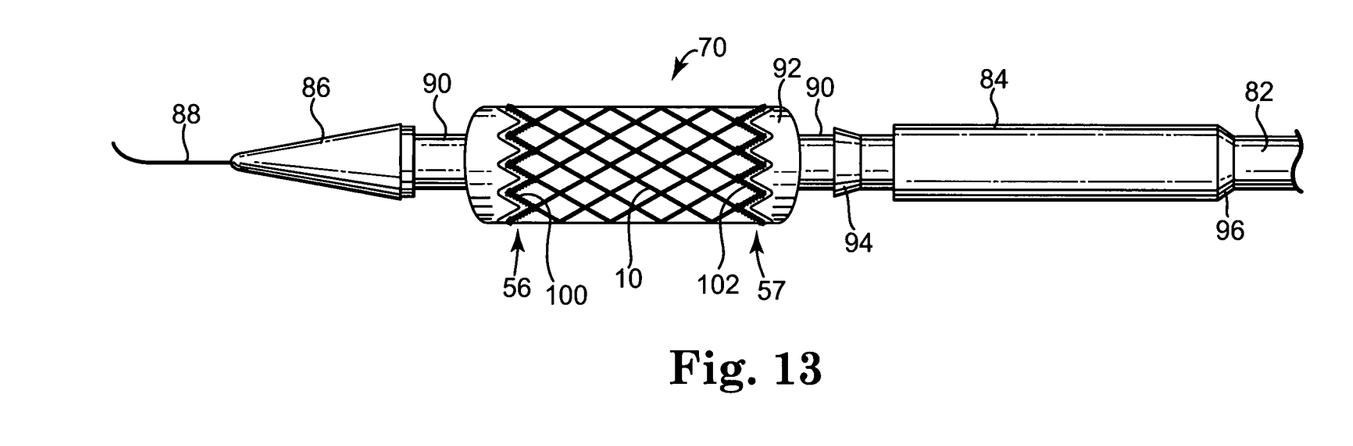
FIG. 13 is a top view illustrating an exemplary operation of the delivery system of FIG. 12.

FIG. 13 illustrates an exemplary mechanism for deployment of the stented valve 70. The outer sheath 82 is moved proximally, exposing a balloon 92 mounted on an inner catheter 90. The balloon 92 can then be expanded, thereby expanding stented valve 70 against the inner surface of the previously implanted adapter stent, stabilizing and sealing the venous segment within the adapter stent. The balloon can then be deflated and the delivery system withdrawn proximally.

In the case of a stented valve made using bovine jugular vein or other preserved biological tissue, the stented valve can be sterilized, stored and shipped separately in a buffered glutaraldehyde solution, but typically not pre-mounted on the delivery system. However, it is possible that the stented valve can also be pre-mounted on the delivery system if the system with a valve mounted thereon is similarly sterilized and kept in a sterile environment. In many cases, however, the implanting physician or an assistant will perform the step of mounting the stented valve 70 to the balloon 92. Because it is not always easy to visually determine which end of the valve is the outflow end, there is a possibility that the valve might be placed incorrectly on the balloon, which would result in an unacceptable implantation procedure. In the embodiment illustrated, however, the suturing 100 at the outflow end 56 of the stent 10 is easy to identify because it is blue in color to preferably correspond to a blue color of the adjacent tip 86. So long as the person mounting the valve to the balloon remembers to match the color of the suture material at the outflow end 56 of the stent 10 to the color of the tip 86, the possibility of a mistake is minimal.

In addition, as described in the above-cited Tower, et al. patent applications, the inner catheter 90 may be provided with a collar 94, which is intended to engage the proximal end of expanded distal portion 84 of the outer sheath 82. The collar may be white, corresponding to the sutures 102 that are white or clear, for example, and located at the inflow end 57 of the stent 10 adjacent the collar, further assisting in proper location of the stented valve 70. While the colored markings on the stented valve are provided by means of colored sutures in the preferred embodiment described above, other methods of marking, such as colored inks or dyes or other colored components might be used in substitution for or in addition to colored suture material.

The present invention has now been described with reference to several embodiments thereof. All patents, patent applications, publications and journal articles mentioned herein are incorporated herein by reference in their entirety. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A prosthetic valve, comprising;
an expandable stent comprising a plurality of zigzag ring structures, each of which comprises a plurality of "V" structures, each "V" structure comprising a base between first and second arms, wherein the ring structures are coupled longitudinally to each other so that at least one "V" structure base of each ring structure is attached at a junction to a "V" structure base of an adjacent ring structure:
a replacement valve positioned at least partially within the expandable stent and comprising a substantially tubular valve body wall;
a plurality of sutures attaching the valve body wall to the stent at the first and second ends of the stent; and, at least one intermediate suture located at one of the "V" structure bases between the first and second ends and attaching the "V" structure base to the valve body.

2. A prosthetic valve according to claim 1, wherein the replacement valve comprises a valved vein segment and the valve body wall comprises the wall of the vein segment.

3. A prosthetic valve according to claim 1, wherein sutures are located along the length of at least one of the first and second arms of at least one of the "V" structures.

4. A prosthetic valve according to claim 3, wherein the plurality of "V" structures extend around a circumference of the framework, and wherein sutures secure the stent to the valve body wall at the junctions and along the arms of all of the "V" structures around the circumference along the first end of the stent.

5. A prosthetic valve according to claim 4, wherein the sutures along the first end of the stent comprise visual indicators for differentiating the first end of the stent from the second end of the stent.

6. The prosthetic valve of claim 1, wherein the replacement valve comprises at least one leaflet extending from an inside surface of the valve body wall.

7. The prosthetic valve of claim 6, wherein the replacement valve comprises a plurality of leaflets, each of which extends from the inside surface of the valve body wall to a commissure that defines an outer meeting point of the furthest downstream portions of two adjacent leaflets, and wherein the valve further comprises a sinus area between each adjacent pair of commissures.

8. The prosthetic valve of claim 7, wherein at least one intermediate suture is located at a junction of the stent that is adjacent to one of the sinus areas of the valve.

9. The prosthetic valve of claim 8, further comprising at least one intermediate suture at a junction that is spaced from all of the sinus areas of the valve.

10. The prosthetic valve of claim 9, comprising a plurality of intermediate sutures arranged in a pattern, wherein each of the intermediate sutures attaches a junction of the stent to the valve body to minimize inward bowing of the valve body wall.

11. The prosthetic valve of claim 8, further comprising a plurality of stitches attaching the valve body wall to at least one of the first and second arms of at least one "V" structure that is positioned adjacent to one of the sinus areas of the valve.

12. The prosthetic valve of claim 11, further comprising a plurality of stitches along both of the first and second arms of at least one "V" structure that is positioned adjacent to one of the sinus areas of the valve.

13. The prosthetic valve of claim 1, further comprising an intermediate suture attaching the valve body to the stent at every stent junction between the first and second ends of the stent.

14. A prosthetic valve, comprising;
an expandable stent having first and second ends and having a framework at least partially defined by plural framework sections and plural junctions between framework sections;
a replacement valve positioned at least partially within the expandable stent and comprising a substantially tubular valve body wall and a plurality of leaflets, each of which extends from an inside surface of the valve body wall to a commissure, and wherein the valve comprises a sinus area between each adjacent pair of commissures;
a plurality of sutures attaching the framework to the valve body wall at the first and second ends of the stent; and at least one intermediate suture located at a junction of the stent that is adjacent to one of the sinus areas of the valve.

15. The prosthetic valve of claim 14, wherein the sutures at the first end of the framework have a different color than the sutures at the second end of the framework.

16. The prosthetic valve of claim 14, further comprising a plurality of stitches attaching the valve body wall to at least one of the plural framework sections of the stent that is positioned adjacent to one of the sinus areas of the valve.

17. The prosthetic valve of claim 14, further comprising a plurality of intermediate sutures arranged in a pattern, wherein each of the intermediate sutures attaches a junction of the stent to the valve body wall.

18. A prosthetic valve, comprising:
an expandable stent comprising a plurality of zigzag ring structures, each of which comprises a plurality of V-shaped members, wherein each V-shaped member comprises a base between first and second arms, and wherein the ring structures are coupled longitudinally to each other so that at least one V-shaped member base of each ring structure is attached at a junction to a V-shaped member base of an adjacent ring structure;
a replacement valve positioned at least partially within the expandable stent and comprising a substantially tubular valve body wall; and
a plurality of sutures attaching the framework to the valve body wall at the first and second ends of the stent; and
a plurality of intermediate sutures arranged in a pattern, wherein each of the intermediate sutures attaches a junction of the stent to the valve body wall to minimize inward bowing of the valve body wall relative to the stent.

19. The prosthetic valve of claim 18, wherein the replacement valve further comprises:
a plurality of leaflets, each of which extends from an inside surface of the valve body wall to a commissure;
a sinus area between each adjacent pair of commissures; and
at least one intermediate suture located at a junction of the stent that is adjacent to one of the sinus areas of the valve.

20. The prosthetic valve of claim 19, further comprising a plurality of stitches along both of the first and second arms of at least one V-shaped member that is positioned adjacent to one of the sinus areas of the valve.

* * * * *